United States Patent [19]

Ayres

[11] 4,132,849

[45] Jan. 2, 1979

[54] PROCESS FOR THE PREPARATION OF 3-HYDROXYMETHYL CEPHALOSPORINS

[75] Inventor: Barry E. Ayres, Ickenham, England

[73] Assignee: Glaxo Laboratories Limited, Greenford, England

[21] Appl. No.: 840,249

[22] Filed: Oct. 7, 1977

[30] Foreign Application Priority Data

Oct. 8, 1976 [GB] United Kingdom ............... 42023/76

[51] Int. Cl.$^2$ ........................................... C07D 501/04
[52] U.S. Cl. ....................................... 544/28; 544/30; 424/246; 544/18
[58] Field of Search ................................... 544/30, 28

[56] References Cited

U.S. PATENT DOCUMENTS

| 3,202,656 | 8/1965 | Abraham et al. ..................... 544/30 |
| 3,532,694 | 10/1970 | Somerfield et al. .................. 544/30 |
| 4,038,275 | 7/1977 | Koppel et al. ................... 260/243 C |

*Primary Examiner*—Nicholas S. Rizzo
*Attorney, Agent, or Firm*—Bacon & Thomas

[57] ABSTRACT

A process for the preparation of a 3-hydroxymethyl cephalosporin compound which comprises selectively hydrolyzing a 3-formyloxymethyl cephalosporin compound under acidic conditions in the presence of a protic solvent whereby a 3-hydroxymethyl cephalosporin is produced.

9 Claims, No Drawings

PROCESS FOR THE PREPARATION OF 3-HYDROXYMETHYL CEPHALOSPORINS

This invention relates to the preparation of cephalosporin compounds and is particularly concerned with the preparation of 3-hydroxymethyl cephalosporins.

The cephalosporin compounds referred to in this specification are generally named with reference to "cepham" (J. Am. Chem. Soc. 1962, 84, 3400). The term "cephem" refers to the cepham structure with one double bond.

3-Hydroxymethyl cephalosporin compounds are valuable intermediates in the synthesis of a range of cephalosporin antibiotics possessing substituted methyl groups at the 3-position by virtue of the chemical reactivity of the hydroxyl group and the consequent ease with which the hydroxymethyl group may be converted to a desired 3-(substituted methyl) group. In particular they are of value in the manufacture of 3-carbamoyloxymethyl and 3-(N-substituted)carbamoyloxymethyl cephalosporin antibiotics.

The preparation of 3-hydroxymethyl cephalosporin compounds has attracted a great deal of attention not only because of the value of such compounds but also because of the difficulty in making them.

Thus, hydrolysis of 3-acyloxymethylceph-3-em-4-carboxylic acids and their esters to their 3-hydroxymethyl analogues by chemical methods has proved to be generally impractical. Base catalysed hydrolysis may lead to opening of the β-lactam ring and acid catalysed hydrolysis may be accompanied by rapid and substantially irreversible lactonisation involving reaction of the 3-hydroxymethyl and 4-carboxy groups.

In British Pat. No. 1,474,519 we have described how esterases obtained from yeast microorganisms of the genus *Rhodotorula* and mutants thereof promote hydrolysis of 3-acyloxymethylceph-3-em-4-carboxylic acids to their 3-hydroxymethyl analogues in good yield. However this enzymatic hydrolysis is only effective with cephalosporin compounds having a free carboxy group in the 4-position whereas it is frequently desired to prepare 3-hydroxymethyl cephalosporin compounds possessing a carboxylate ester group in the 4-position.

There is thus a need for alternative sources and methods of obtaining 3-hydroxymethyl cephalosporin compounds.

We have now found that 3-formyloxymethyl cephalosporin compounds may be converted to 3-hydroxymethyl cephalosporin compounds in good yield. This finding is important because 3-formyloxymethyl cephalosporins may in turn be derived in a multi-stage process from penicillin compounds. Consequently one is afforded not only a new method of making 3-hydroxymethyl cephalosporin compounds but also an alternative source to existing methods relying on fermentation produced 3-acetoxymethyl cephalosporin compounds.

This multi-stage process may be shown schematically as follows:

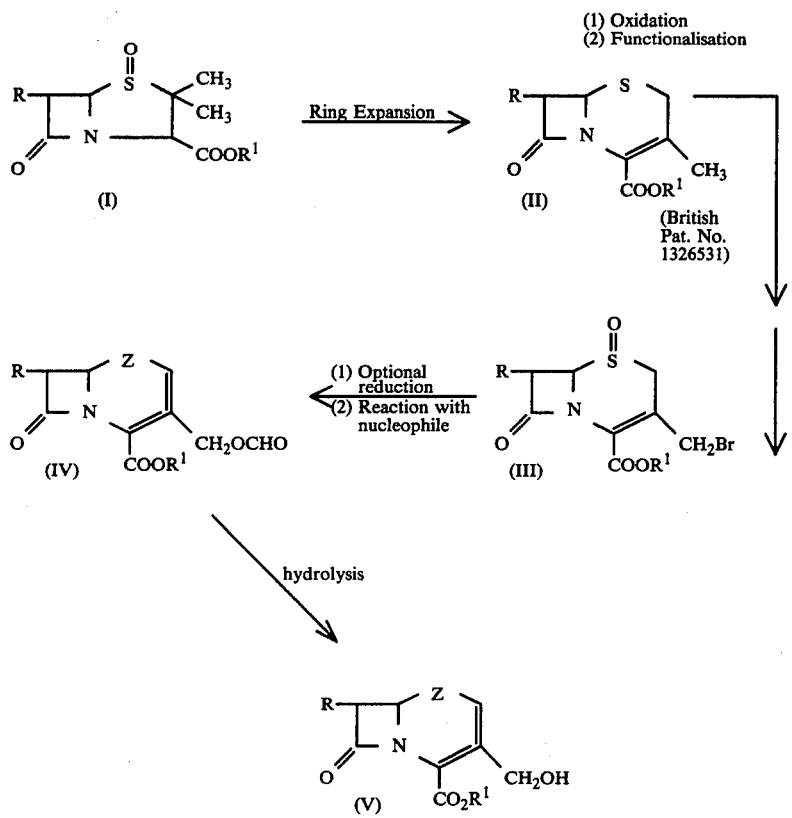

where R is a blocked amino group, preferably a $C_1$-$C_{20}$ acylamido groups, Z is $>S$ or $>S\rightarrow O$, $R^1$ is a carboxyl blocking group and the dotted line bridging the 2-, 3- and 4-positions indicates that the compound may be a ceph-2-em or ceph-3-em compound).

If $Z = >S\rightarrow O$ the end-product is obtained as a ceph-3-em compound for direct use in subsequent reactions since the multi-stage process does not produce any substantial quantity of ceph-2-em isomers. If $Z = S$, the $\Delta^3$ product may be accompanied by some of its $\Delta^2$ isomer. In this event, or if the use of $\Delta^2$ intermediates is desired, $\Delta^3$ compounds may subsequently be produced by standard methods of sulphoxidation and reduction. In general, therefore, Z is preferably $>S\rightarrow O$.

According to one embodiment of the invention there is provided a process for the preparation of a 3-hydroxymethyl cephalosporin compound which comprises selectively hydrolysing a 3-formyloxmethyl cephalosporin compound under acidic conditions in association with a protic solvent, preferably in the presence of an inert diluent, and advantageously at a temperature within the range of 0°–50° C., preferably 15°–40° C.

Any functional groups in the 3-formyloxymethyl cephalosporin may be protected during the hydrolysis reaction e.g. as is indicated in the above schematic representation of the multi-stage process.

The hydrolysis is advantageously effected using an acid having a pKa of less than 4, such as sulphuric, phosphoric, perchloric, hydrochloric, trifluoroacetic, p-toluene sulphonic, hydrobromic, nitric, formic or oxalic acid or an alkylphosphoric acid (which may, for example, be formed in situ by reaction of phosphorus pentoxide and an alkanol). The acid is preferably employed in a sufficient amount to maintain the pH of the reaction mixture at less than 4, advantageously at a pH of 1 to 3.

The protic solvent may be water or a lower alkanol. Preferably water is employed.

Any inert organic diluent used is preferably miscible with the protic solvent(s) and is preferably one in which the 3-formyloxy methyl cephalosporin is soluble. The diluent is conveniently an organic diluent, preferably dimethyl formamide but examples of other diluents which may be employed include tetrahydrofuran, dioxan, acetone, methanol, dimethylacetamide, dichloromethane, chloroform, industrial methylated spirits, ethylene glycol and ethyl acetate as well as mixtures of two or more thereof.

The hydrolysis is advantageously effected at room temperature using an aqueous hydrochloric acid/dimethylformamide system.

The reaction may be monitored by thin layer chromatography and the 3-hydroxymethyl cephalosporin product of formula V may be isolated for example by extraction or precipitation. Purification may be effected for example by crystallisation, by precipitation or by column chromatography on a suitable adsorbent e.g. silica gel of 60–200 mesh size.

The compounds of general formula (IV), i.e. 3-formyloxymethyl starting compounds, may be prepared in an analogous manner to that described in British Pat. No. 1326531, the halogen of a 3-halomethyl cephalosporin being replaced by a formate anion in a nucleophilic displacement reaction.

Sources of the formate anion may be inorganic or organic formate salts e.g. sodium formate or triethylammonium formate, and the displacement may be carried out in an inert solvent system e.g. acetone or tetrahydrofuran, if necessary with added water to aid the solubility of any ionic reagents. Heavy metals, such as silver and mercury, may also be present to promote the reaction.

The source of the formate group may also be a substituted formamide e.g. N,N-dimethylformamide, which may react directly with the halomethyl compound if desired in the presence of a catalyst such as a mild base (e.g. $NaHCO_3$) or an inorganic salt (e.g. $Na_2SO_3$).

When the 3-formyloxymethyl cephalosporin is prepared in this way, it may be hydrolysed in situ in accordance with this invention, for example, by adding an aqueous acid.

According to a preferred embodiment of the present invention we provide a process for the preparation of a 3-hydroxymethyl cephalosporin compound of formula

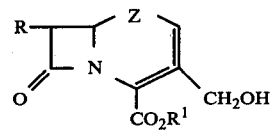

V (wherein R is a blocked amino group, preferably a $C_1$–$C_{20}$ acylamido group, Z is $>S$ or $>S\rightarrow O$, $R^1$ is a carboxyl blocking group and the dotted line bridging the 2-, 3- and 4-positions indicates that the compound may be a ceph-2-em or ceph-3-em compound) in which a 3-formyloxymethyl cephalosporin compound of formula

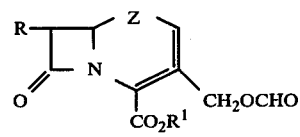

IV (wherein R, Z, $R^1$ and the dotted line are as defined above) is selectively hydrolysed, whereafter, if desired in each instance, any of the following reactions are carried out:

(i) conversion of a $\Delta^2$ isomer into the corresponding $\Delta^3$ isomer (ii) reduction of a compound in which Z is $>S\rightarrow O$ to form a compound in which Z is $>S$; and (iii) removal of any carboxyl blocking groups.

The acyl moiety of R may be selected from the extensive lists of such acyl groups in the penicillin and cephalosporin literature. Specific acyl groups are illustrated in the accompanying list, which is not intended to be exhaustive:

(i) $R^uC_nH_{2n}CO$- where $R^u$ is aryl (carbocyclic or heterocyclic), cycloalkyl, substituted aryl, substituted cycloalkyl, cycloalkadienyl, or a non-aromatic heterocyclic or mesoionic group and n is 0 or an integer from 1–4. Examples of this group include phenylacetyl; thien-2- and -3-ylacetyl, 3- and 4-isoxazolylacetyl both substituted or unsubstituted; pyridylacetyl, tetrazolylacetyl or a sydnoneacetyl group. Where n is other than 0, especially when n is 1, the α-carbon atom of the acyl group may be substituted by, for example, a hydroxy, esterified hydroxy (e.g. lower alkanoyloxy such as acetoxy), blocked amino (e.g. amino substituted by any of the blocking groups specified hereinafter), hydroxyimino, acyloxyimino (e.g. lower alkanoyloxyimino such as acetoxyimino or halo-substituted lower alkanoyloxyimino such as mono- or dichloroacetoxyimino) or etherified oxyimino (e.g. lower alkoxyimino such as methoxyimino or t-butoxyimino, lower cycloalkyloxyimino such as cyclopentyloxyimino or aryloxyimino such as phenoxyimino) group; examples of α-substituted acyl groups of this type include 2-hydroxy-2-phenylacetyl, N-blocked 2-amino-2-phenylacetyl and 2-(fur-2-yl)-2-hydroxyiminoacetyl.

(ii) $C_nH_{2n+1}CO-$ where n is 0 or an integer from 1–7. The alkyl group may be straight or branched and may be substituted by e.g. a cyano group, a carboxy group, an alkoxycarbonyl group, a hydroxy group, a blocked amino group or a carboxycarbonyl group (—CO.COOH) or any such group in which the functional group is blocked. Examples of such groups include formyl, glutaroyl, and N-blocked (e.g. N-ethoxycarbonyl) R-5-amino-5-carboxypentanoyl.

(iii)

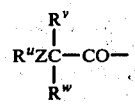

where $R^u$ has the meaning defined under (i) and in addition may be benzyl, and $R^v$ and $R^w$ which may be the same or different each represent hydrogen, phenyl, benzyl, phenethyl, or lower alkyl and Z is an oxygen or sulphur atom. Examples of this group include phenoxyacetyl or pyridylthioacetyl.

The carboxyl blocking group $R^1$ is desirably a group which may readily be split off at a suitable stage. It may, however, be convenient in some instances to employ biologically acceptable, metabolically labile carboxyl blocking groups and retain these in the final product.

Suitable carboxyl blocking groups are well known in the art, a list of representative blocked carboxyl groups being included in Belgian Patent No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; for instance by acid catalysis (e.g. with anhydrous trifluoroacetic acid) or by reduction (e.g. by hydrogenation) or by enzymically-catalysed hydrolyses.

In order that the invention may be well understood the following examples are given by way of illustration.

All temperatures are quoted in ° C. Melting points were measured in capillary tubes, the values are uncorrected.

Petrol is petroleum b.p. 40° to 60°.

T.l.c. is thin-layer chromatography using pre-coated plates (Merck $F_{254}$, 0.25mm thick coating) which were examined under ultraviolet light at 254nm and were developed with iodine.

EXAMPLE 1

(a) Diphenylmethyl(1S,6R,7R)-3-Bromomethyl-7-phenoxyacetamidoceph-3-em-4-carboxylate, 1-oxide A cooled (−9°) solution of diphenylmethyl (1S,6R,7R)-3-methyl-7-phenoxyacetamidoceph-3-em-4-carboxylate, 1-oxide (9.70mmole) in dichloroethane (250ml) was stirred with 1,3-dibromo-5,5-dimethylhydantoin (2.08g, 7.28mmole) under a nitrogen atomsphere.

The mixture was irradiated with ultra-violet light (from a 125 watt Hanovia mercury arc lamp) at −9° for 1 hour, filtered, washed with 3% sodium bicarbonate solution (2×100ml) and water (50ml), then dried and concentrated giving the crude title compound (2.87g) as a solid, $[\alpha]_D$ − 53° (c 0.94, DMSO), $\lambda_{max}$ (EtOH) 268.5nm ($\epsilon$ 9,255), 274.5 ($\epsilon$ 9,930) with inflection at 264($\epsilon$ 8,045) and 280nm ($\epsilon$ 9,260) respectively.

Chromatography of the filtrate afforded a further crop of the title compound (348mg).

(b) Diphenylmethyl (1S,6R,7R)-3-formyloxymethyl-7-phenoxyacetamidoceph-3-em-4-carboxylate 1-oxide A suspension of sodium sulphite heptahydrate (103mg, 0.41mmole) in N,N dimethylformamide (1ml) was treated with urea (100mg) but the sodium sulphite did not dissolve appreciably.

Diphenylmethyl(1S,6R,7R)-3-bromoethyl-7-phenoxyacetamidoceph-3-em-4-carboxylate, 1-oxide (244mg, 0.40mmole) was added to the above mixture which was stirred at 20° for 24 hours and allowed to stand at 20° for a further 2½ days by which time t.l.c. showed complete reaction.

The stirred solution (containing very little residue) was diluted with water (20ml) and the mixture was stirred at 20° for 30 minutes, the resultant brown precipitate was filtered off and washed with water and dried in vacuo to give the crude title compound (151mg), m.p. 122 to 140° $[\alpha]_D^{22}$ +36° (c 0.64, $CHCL_3$), $\lambda_{max}$(EtOH) 269nm ($E_{1cm}^{1\%}$ 138, $\epsilon$ 7,940) and 274.5nm ($E_{1cm}^{1\%}$ 122, $\epsilon$ 7,020) with an inflection at 266nm ($E_{1cm}^{1\%}$ 132, $\epsilon$7,600).

(c) Diphenylmethyl (1S,6R,7R)-3-hydroxymethyl-7-phenoxyacetamidoceph-3-em-4-carboxylate, 1-oxide To a warmed (<30°) stirred suspension of diphenylmethyl (1S,6R,7R)-3-formyloxymethyl-7-phenoxyacetamidoceph-3-em-4-carboxylate, 1-oxide (400mg, 0.7mmole) in methanol (40ml) was added perchloric acid (60%; 0.1ml, 0.9mmole). The mixture was stirred at 25° for 45 minutes then dichloromethane (12ml) was added and the solution was stirred at 25° for 5 minutes then partitioned between dichloromethane and water. The organic layer was separated and washed with water and dried (sodium sulphate) and evaporated in vacuo to a brown residue (382 mg) which, on trituration with ether-petrol (1:2) gave the crude title compound (312mg), as an amorphous orange solid, m.p. 92 to 150° C., $[\alpha]_D^{22}$ +36°($CHCL_3$, c 0.49).

A sample of the crude title compound (150mg) was subjected to column chromatography on silica-gel (Crosfield 60 to 200 mesh, 10g); elution was with ethyl acetate and 15ml fractions were collected. Fractions 2 to 7 were combined and evaporated in vacuo to an off-white solid (80mg) which, on trituration with ether, afforded the title compound (52mg) as an off-white solid, m.p. 181 to 184° $[\alpha]_D^{22}$ + 19.5° ($CHCl_3$, c 0.41) $\lambda_{max}$ (EtOH) 263nm ($E_{1cm}^{1\%}$ 158, $\epsilon$8,650) with inflections at 266nm ($E_{1cm}^{1\%}$ 156, $\epsilon$ 8,500) and 274mn ($E_{1cm}^{1\%}$ 116, $\epsilon$ 6,350) [Found C, 62.6; H, 4.6; N,5.4. $C_{29}H_{26}N_2O_7S$ ½$H_2O$ requires C, 62.7; H 4.9; N, 5.05%].

EXAMPLE 2

(a) t-Butyl (1S,6R,7R)-3-formyloxymethyl-7-phenoxyacetamidoceph-3-em-4-carboxylate, 1-oxide t-Butyl (1S,6R,7R)-3-bromomethyl-7-phenoxyacetamidoceph-3-em-4-carboxylate, 1-oxide (500mg, 1mmole) in acetone (20ml) was treated with formic acid (0.25ml) and triethylamine (0.5ml) and the reaction solution was stirred at 30° to 40° for 4 hours, and then left to stand at 20° for 18 hours. The solution was concentrated by evaporation and then partitioned between ethyl acetate and water. The organic layer was washed with water, and dried over sodium sulphate and evaporated to a brown oil (450mg). The oil in ethyl acetate (~10ml) was filtered and the filtrate was added slowly to well stirred petrol (~120ml). The precipitate was filtered off and dried in vacuo to give the title compound (338mg) as a pale brown solid. [α]D + 45° (CHCl$_3$, c 0.51%), λinf266nm (ε9250), λmax 268.5nm (ε9530), λmax 273nm (ε8460) (ethanol) [Found: C, 54.25; H, 5.2; N, 5.7; S, 6.9. $C_{21}H_{24}N_2O_8S$ requires C, 54.3; H, 5.2; N, 6.1; S, 6.9%]. cl (b) t-Butyl (1S,6R,7R)-3-hydroxymethyl-7-phenoxyacetamidoceph-3-em-4-carboxylate, 1-oxide t-Butyl (1S,6R,7R)-3-formyloxymethyl-7-phenoxyacetamidoceph-3-em-4-carboxylate, 1-oxide (50mg, 0.11mmole) in methanol (5ml) was treated with 2N hydrochloric acid (0.025ml,0.05mmole) and the solution was stirred at 24° for 2 hours. Propylene oxide (0.1ml) was then added, and the mixture was stirred at 24° for 3 minutes and then partitioned between ethyl acetate and water. The organic layer was washed with water and dried over sodium sulphate and evaporated to an oil (47mg, 100%). A solution of the oil in ethyl acetate (2ml) was added slowly to stirred petrol (100ml) and the white precipitate was filtered off and dried in vacuo to give the title compound (31mg, 66%) as a white solid, [α]$_D$ + 56° (CHCl$_3$,c 0.21%), > 90% pure by t.l.c. and n.m.r.

EXAMPLE 3

Diphenylmethyl (1S,6R,7R)-3-hydroxymethyl-7-phenoxyacetamidoceph-3-em-4-carboxylate, 1-oxide Diphenylmethyl (1S,6R,7R)-3-formyloxymethyl-7-phenoxyacetamidoceph-3-em-4-carboxylate, 1-oxide (50mg, 0.087mmole) was suspended in methanol (5ml) and 2N hydrochloric acid (0.02ml, 0.04mmole) was added. The suspension was stirred at 27° for 3.5 hours, during which time it became a homogeneous solution of apparent pH ca 2-3. Propylene oxide (0.1 ml) was added, and after two minutes the solution was partitioned between ethyl acetate and water. The organic layer was washed with water and dried over anhydrous sodium sulphate and evaporated to an oily foam (49mg). A solution of the foam in ethyl acetate (2ml) was added to stirred 40°-60° petroleum ether (100ml) and the precipitate was filtered off and dried in vacuo to give the slightly impure title compound (28mg) as an off-white solid, [α]$_D^{22}$ + 37° (CHCl$_3$, c 0.21%). The product appeared (by t.l.c. and n.m.r.) to contain about 10 to 20% of lactone impurity.

EXAMPLE 4

Diphenylmethyl (1S,6R,7R)-3-hydroxymethyl-7-phenoxyacetamidoceph-3-em-4-carboxylate, 1-oxide (i) variation of acid catalyst Diphenylmethyl (1S,6R,7R)-3-formyloxymethyl-7-phenoxyacetamidoceph-3-em-4-carboxylate, 1-oxide (25mg) in methanol (5ml) was treated with one or two molar equivalents (see Table below) of the specified acid at 30°. The reaction was judged to be complete when there was only a trace, if any, of the 3-formyloxymethyl starting material by thin-layer chromatography (t.l.c.), and the ratio of products in the final reaction mixture was determined by the t.l.c. (silica plates eluted with ethyl acetate). The approximate $R_f$ values of the components were: 3-formyloxymethyl starting material: 0.65; title compound: 0.55; and corresponding lactone: 0.1. The apparent pH of the reaction mixture was determined by spotting an aliquot on to moistened universal pH indicator paper.

TABLE

| Acid used | Molar equivalents of acid | Time for Complete reaction | Amount of lactone in final reaction mixture | Apparent pH of reaction |
| --- | --- | --- | --- | --- |
| 20% aq. HNO$_3$ | 1 | 2 hr | trace | 2 |
| phosphorus pentoxide P$_2$O$_5$ | 1 | 2 hr | ~ 10% | 2.5 |
| trichloroacetic acid CCl$_3$CO$_2$H | 1 | 19 hr | ~ 10% | 3.5 |
| H$_3$PO$_4$ (orthophosphoric acid) | 2 | 48 hr | trace | 3 – 4 |
| oxalic acid (CO$_2$H)$_2$ . 2H$_2$O | 2 | 4 days | trace | 3 – 4 |

(ii) Variation of solvent

The same conditions were used as in (i) above except that the specified solvent was used in place of methanol; the results are set out in the Table below:

| Solvent used | Amount of solvent | Acid used | Molar eq. of acid | Time for complete reaction | Amount of lactone in final mixture | App. pH of reaction |
| --- | --- | --- | --- | --- | --- | --- |
| 1,2-ethanediol | 5 ml | 2N hydrochloric acid | 1 | 7½ hr | ~ 20% | ~ 3 |
| acetone | 1 ml | " | 2 | 5 hr | ~ 10% | 1.5 |
| tetrahydrofuran | 1 ml | " | 4 | 4 hr | ~ 10% | ~ 1 |
| N,N-dimethylformamide | 1 ml | " | 4 | 24 hr | trace | 3 |

(iii) Variation of reaction conditions

The above 3-formyloxymethyl starting material was dissolved in the specified solvent or solvent mixture and treated with the specified acid, as indicated in the Table below. When t.l.c. indicated complete reation [as in (i) above] the product was isolated by the work-up described, and its purity was assessed by t.l.c. [as in (i) above]. The n.m.r. spectrum of each product agreed with the spectrum of the authentic material, plus an amount of lactone roughly in accord with the amount observed by t.l.c. The optical rotation of an impure sample of the lactone in chloroform (+94°) was considerably higher than that of the authentic 3-hydroxymethyl compound (+19.5°). The purity of each product could therefore be estimated from its rotation, and this estimate was consistent with those from the other methods mentioned above. The details of the reactions are summarised in the Table below.

| 3-formyl-oxymethyl Compound (mg) | Solvent (ml) | Acid (ml) | Molar equiv. of acid | pH of reaction | Reaction time | Work-up | Isolated Prod. Wt. | Isolated Prod. Yield | % Lactone t.l.c. | [α]$_D^{22}$ (CHCl$_3$) |
|---|---|---|---|---|---|---|---|---|---|---|
| 50 | Acetone (0.5) Methanol (1.0) | 2N hydrochloric acid (0.1ml) | 2.3 | 1.5 | 1¾ hr | A | 35mg | 74% | <10% | +20° |
| 50 | Dichloromethane (0.5) Methanol (1.0) | 2N hydrochloric acid (0.025 ml) | 0.6 | ~2 | 3 hr | B | .32mg | 67% | ~10% | +32° |
| 50 | Acetone (0.5) Methanol (1.0) | 2N Sulphuric acid (0.025ml) | 0.3 | 2 to 3 | 5 hr 40m | C | 32mg | 67% | ~10% | +32° |
| 200 | Methylated spirit (Industrial) (10.0) Dichloromethane (3.0) | 6N hydrochloric acid (0.05ml) | 0.9 | ~2.5 | 4½ hr | D | 177mg | 93% | 10-20% | +36° |
| 100 | N,N-Dimethylformamide (2.0) | 2N hydrochloric acid (0.36 ml) | 4 | 2 to 3 | 6 hr | A | 71mg | 75% | <5% | +23° |
| 200 | N,N-Dimethylformamide (1.0) | 2N hydrochloric acid (0.1ml) | 0.55 | 3 | 24 hr | E | 164 mg | 86% | <5% | +23° |

NOTES TO TABLE

WORK UP

A. Propylene oxide (in excess) (0.1 to 0.4 ml) was added and the mixture was stirred for 5 minutes and then partitioned between ethyl acetate (ca 75 ml) and water (ca 75 ml). The organic layer was washed with water (2 × ca 50 ml) and dried over anhydrous sodium sulphate and filtered and evaporated to ca 3 to 5 ml. This solution was added dropwise to stirred 40°–60° petroleum ether (ca 150 ml). The resulting precipitate was filtered off and dried in vacuo.

B. As above for A but dichloromethane was used in place of ethyl acetate.

C. As above for A but no propylene oxide was added.

D. Saturated aqueous sodium hydrogen carbonate solution (0.3 ml) was added and the resulting mixture was concentrated to about 0.75 of its volume. This mixture was partitioned between ethyl acetate (75 ml) and water (75 ml). The organic layer was washed with water (2 × 75 ml) and dried over anhydrous sodium sulphate and filtered and then evaporated to a foam.

E. Propylene oxide (0.05 ml) was added and the mixture was stirred for 3 minutes. Water (20 ml) was added and the resulting solid was filtered off, washed with water (2 × 10 ml), dried on the sinter for 5 minutes and then dried in vacuo.

EXAMPLE 5 t-Butyl (6R,7R)-3-Hydroxymethyl-7-(2-thienylacetamido)-ceph-2-em-4-carboxylate t-Butyl (6R,7R)-3-formyloxymethyl-7-(2-thienylacetamido)ceph-2-em-4-carboxylate (50 mg.; 0.115 mmole), warm methanol (2 ml) and 2N hydrochloric acid (0.025 ml) were stirred together at 25° C. at an apparent pH of 2. T.l.c. after 2 hours 20 minutes showed a virtually complete reaction. Propylene oxide (0.1 ml) was added and the mixture was stirred at 25° C. for 5 minutes. The mixture was partitioned between ethyl acetate (40 ml) and water (40 ml). The aqueous layer was extracted with ethyl acetate (20 ml) and the combined organic layers were washed with water (2 × 20 ml) and dried over anhydrous sodium sulphate and filtered and evaporated to a gum. This gum was dissolved in ethyl acetate (2 ml) and added dropwise to stirred 40 to 60° petroleum ether (100 ml) to give a pale yellow solid (23mg.; 50%). T.l.c. after work up indicated approximately 20% lactone. τ (d$^6$DMSO) 0.81 (d, J 9Hz; NH), 2.6, 3.0 (mult.; thienyls), 3.5 (broad s; Δ$^2$ 2-H), 4.51 (d,d J 9, 5Hz; 7-H), 4.80 (d, J 5Hz; 6-H), 4.92 (broad s; —CH$_2$OH), 5.10 (broad s; 4-H), 5.95 (mult; 3 CH$_2$), 6.20 (s;

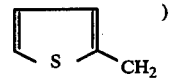

and 8.55 (s; tBu).

EXAMPLE 6

Diphenylmethyl (1S,6R,7R)-7-Formamido-3-hydroxymethylceph-3-em-4-carboxylate, 1-oxide (a) Diphenylmethyl (1S,6R,7R)-7-formamido-3-formyloxymethylceph-3-em-4-carboxylate, 1-oxide (100mg) in N,N-dimethylformamide (2 ml) was treated with 2N hydrochloric acid (0.05 ml) and the solution was stirred at 25° for 22 hours, during which time the apparent pH of the reaction rose from about 3.0 to about 3.5. More 2N hydrochloric acid (0.02 ml) was added, and the solution was stirred for 6 hours and then left to stand (at 25°) for 60 hours. Propylene oxide (0.07 ml) was added and the solution was stirred at 25° for 5 minutes, and it was then partitioned between ethyl acetate (50 ml) and water (50 ml). The organic layer was washed with water (50 ml) and dried over sodium sulphate and filtered and evaporated to a gum which was suspended in ethyl acetate (8 ml) and added slowly to stirred 40° to 60° petroleum ether (100 ml). The flocculent precipitate was filtered off and dried in vacuo to give the title compound (47 mg) as a pale brown solid.

T.l.c. (elution with ethyl acetate/acetic acid 9/1 or with chloroform/methanol/acetic acid 90/16/20) and n.m.r. showed the product to contain some unchanged formate ester (~10%), but no discernable amount of lactone: τ (DMSO-d₆) 1.63 (d, J 9, NH), 1.81 (s, HCO), ca 2.3 to b 2.9 (m, Ph₂), 3.08 (s, CHPh₂), 3.99 (dd, J 5.9, 7-H), 4.85 (m, OH), 5.02 (d, J5, 7-H), 5.57 and 5.82 (ABqm, J14, 3-CH₂), 5.98 and 6.38 (ABq, J 18, 2-H₂)

(b) The procedure described in (a) above was repeated except that the product was isolated (after the 60 hour reaction period) by adding water (20 ml) and filtering off and drying (in vacuo) the precipitate. This yielded the title compound (49 mg) as a buff-coloured solid. T.l.c. and n.m.r. showed the product to contain some unchanged formate ester (<10%), but no discernable amount of lactone: the n.m.r. resembled that of the product from part (a) above.

(c) Diphenylmethyl (1S,6R,7R)-7-formamido-3-formyloxymethylceph-3-em-4-carboxylate, 1-oxide (127 mg, 0.25 mmole) was suspended in methanol (5ml) and perchloric acid (60%, 0.015 ml, 0.13 mmole) was added. The suspension was stirred at 30° for 75 minutes, but no reaction appeared to occur (by t.l.c.). Chloroform (5ml) was added and the mixture (still not all in solution) was stirred at 30° for 4 hour, by which time a solution had formed. The solution was partitioned between chloroform and water, and the organic layer was washed with water and dried over sodium sulphate and filtered and evaporated to a foam (80mg) which was triturated with ether to give the title compound (51 mg) as a light brown solid.

T.l.c. and n.m.r. showed the product to contain small amounts of the formate ester (10–20%) and the lactone (<5%): $\nu_{max}$ (CHBr₃) ca 3600 (OH), 3400 (NH), 1798 (β-lactam), 1725 (CO₂R), 1692 and 1500 (CONH) and 1042 cm⁻¹ (sulphoxide). The NMR spectrum resembled that in preparation (a) above.

Preparation 1

Diphenylmethyl (1S, 6R, 7R)-7-Formamido-3-formyloxymethylceph-3 em-4-carboxylate, 1-oxide Diphenylmethyl (1S, 6R, 7R)-3-Bromomethyl-7-formamidoceph-3-em-4-carboxylate, 1-oxide (503 mg - 1 mmole) was suspended in acetone (10 ml) and to the vigorously stirred mixture was added formic acid (0.4 ml; ca 10 mmole) and triethylamine (0.8 ml; ca 6 mmole). The stirred mixture was warmed to 45° and then allowed to cool to room temperature (30°) over 1 hour. (A thick buff coloured precipitate was formed over ½ hour). The mixture was stirred at 30° for a further 1¼ hours, when t.l.c. showed a complete reaction, and then it was slowly diluted with water (20 ml). The fine pale-brown precipitate was filtered off, washed with water and dried in vacuo to give the title compound (361 L mg) m.p. 198° to 200° (decomp.) $[\alpha]_D$ +34° (DMSO, c 0.87%)λmax (chloroform) 269.5 mm (ε8,650), νmax (CHBr₃) 3320, 3280 (NH), 1788 (β-lactam), 1720,1710(shoulder) (ester, OCHO), 1660, 1655 (shoulder) and 1535 cm⁻¹ (amide).

Preparation 2 t-Butyl (6R, 7R)-3-Formyloxymethyl-7-(2-thienylacetamido) ceph-2-em-4-carboxylate t-Butyl (6R, 7R)-3-Bromomethyl-7-(2-thienylacetamido) ceph-2-em-4-carboxylate (592 mg; 1.25 mmole), acetone (25 ml), 98–100% formic acid (0.25 ml; 6.25 mmole; 5.0 molar equivalents) and triethylamine (0.5 ml; 3.75 mmole; 3.0 molar equivalents) were stirred together at 25° C. under nitrogen. Acetone (10ml) was added, but a suspension was still formed. The mixture was stirred for 22½ hours when t.l.c. (ethyl acetate:toluene 1:1) showed a complete reaction. The mixture was concentrated to ¼ it's volume and poured into swirling water (125 ml). The resulting precipitate was extracted into ethyl acetate (1 × 75 ml; 1 × 20 ml). The yellow organic layer was washed with water (1 × 75 ml) and dried over anhydrous sodium sulphate and filtered. The filtrate was stirred with charcoal for ½ hour. The mixture was filtered through kieselguhr, the cake washed with ethyl acetate, and then the filtrate was evaporated to a pale yellow gum, the title compound (242mg) $[\alpha]_D^{21}$ + 264° (CHCl₃; c 0.53%), λmax (ethanol) 237 nm (ε14,600), νmax (CHBr₃) 3400 (NH), 1770 (β-lactam), 1720 (ester) 1675 and 1500 cm⁻¹ (amide).

I claim:

1. A process for the preparation of a compound of the formula

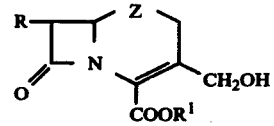

wherein Z is > S or > S→O, R is a blocked amino group and R¹ is a carboxyl blocking group, which comprises selectively hydrolysing under acidic conditions in the presence of a protic solvent selected from the group consisting of water and a lower alkanol, a compound of the formula

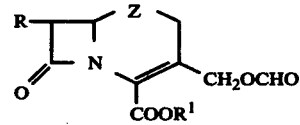

wherein Z, R and R¹ have the meanings given above.

2. A process as claimed in claim 1 wherein the hydrolysis is effected at a pH of less than 4.

3. A process as claimed in claim 2 wherein the hydrolysis is effected at a pH of 1 to 3.

4. A process as claimed in claim 1 wherein the hydrolysis is effected using an acid having a pKa of less than 4.

5. A process as claimed in claim 4 wherein the said acid is sulphuric, phosphoric, perchloric, hydrochloric, trifluoroacetic, p-toluene-sulphonic acid, hydrobromic, nitric, formic or oxalic acid or an alkyl-phosphoric acid.

6. A process as claimed in claim 1 wherein the hydrolysis is effected in dimethylformamide as an inert diluent.

7. A process as claimed in claim 1 wherein the hydrolysis is effected at a temperature of 0–50° C.

8. A process as claimed in claim 1 in which Z is =S→O.

9. A process as claimed in claim 1 in which hydrolysis is effected using an aqueous hydrochloric acid/dimethylformamide system.